United States Patent [19]

Böttcher et al.

[11] Patent Number: 4,916,143

[45] Date of Patent: Apr. 10, 1990

[54] HYDROXYINDOLE ESTERS

[75] Inventors: Henning Böttcher, Darmstadt; Christoph Seyfried, Seeheim-Jugenheim; Klaus-Otto Minck, Ober-Ramstadt, all of Fed. Rep. of Germany

[73] Assignee: Merck Patent Gesellschaft Mit Beschrankter Haftung, Darmstadt, Fed. Rep. of Germany

[21] Appl. No.: 228,150

[22] Filed: Aug. 4, 1988

Related U.S. Application Data

[63] Continuation of Ser. No. 15,198, Feb. 17, 1987, abandoned.

[30] Foreign Application Priority Data

Feb. 17, 1986 [DE] Fed. Rep. of Germany ....... 3604949

[51] Int. Cl.$^4$ .................. C07D 401/06; C07D 401/12; A61K 31/40; A61K 31/445
[52] U.S. Cl. ...................................... 514/323; 546/201
[58] Field of Search .......................... 546/201; 514/323

[56] References Cited

U.S. PATENT DOCUMENTS 3,075,992  1/1963  Hofmann et al. .................... 546/201
4,576,940  3/1986  Tahara et al. .................... 548/557 X

FOREIGN PATENT DOCUMENTS

3342632A1  6/1985  Fed. Rep. of Germany .

OTHER PUBLICATIONS

Costall et al., European Journal of Pharmacology, 50 (1978), 39–50, "Climbing Behaviour Induced by Apomorphine . . . ".

Lassen, Acta Pharmacol et toxicol, 1979, 45, 161–165, "Inhibition of Apomorphine–Induced Climbing in Mice . . . ".

Protais et al., Psychopharmacology 50, 1–6 (1976), "Climbing Behavior Induced by Apomorphine in Mice: A Simple Test . . . ".

Primary Examiner—Joseph Paul Brust
Attorney, Agent, or Firm—Millen, White & Zelano

[57] ABSTRACT

Hydroxyindole esters of the formula

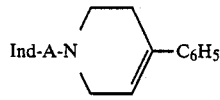

wherein
Ind is 3-indolyl substituted in the 4-, 5-, 6- or 7-position by acyloxy having 1–12 C atoms,
A is —(CH$_2$)$_4$— or —CH$_2$—SO$_n$—CH$_2$ $_{CH2}$— and
n is 0, 1 or 2, or physiologically acceptable salts thereof exhibit effects on the central nervous system.

8 Claims, No Drawings

HYDROXYINDOLE ESTERS

This is a continuation of application Ser. No. 07/015,198 filed Feb. 17, 1987, now abandoned.

BACKGROUND OF THE INVENTION

This invention relates to hydroxyindole esters and physiologically acceptable salts thereof.

SUMMARY OF THE INVENTION

It is an object of this invention to provide new compounds which can be used for the preparation of medicaments.

Upon further study of the specification and appended claims, further objects and advantages of this invention will become apparent to those skilled in the art.

These objects have been achieved by providing new hydroxyindole esters of the formula:

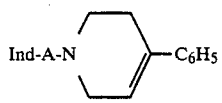

wherein
Ind is a 3-indolyl radical which is substituted in the 4-, 5-, 6- or 7-position by an acyloxy group having 1–12 C atoms,
A is —(CH$_2$)$_4$— or —CH$_2$—SO$_n$—CH$_2$CH$_2$— and
n is 0, 1 or 2, or physiologically acceptable salts thereof.

DETAILED DISCUSSION

It has been found that the compounds of the formula I and their physiologically acceptable salts posses valuable pharmacological properties. Thus, they display, in particular, effects on the central nervous system, above all dopamine-stimulating, presynaptic (neuroleptic) or post-synaptic (anti-Parkinson) effects. In particular, the compounds of the formula I induce contralateral pivoting behavior in hemiparkinson rats (detectable by the method of Ungerstedt et al., Brain Res. 24 (1970), (485–493) and inhibit the binding of tritiated dopamine-agonists and dopamine-antagonists to extrapyramidal receptors (detectable by the method of Schwarcz et al., J. Neurochemistry 34 (1980), (772–778), and Creese et al., European J. Pharmacol. 46 (1977), (377–381). In addition, the compounds inhibit the linguomandibular reflex in narcotized rats (detectable by a method based on the methods of Barnett et al., Eurpoean J. Pharmacol. 21 (1973), 178–182 and of Ilhan et al., European J. Pharmacol. 33 (1975), (61–64). Analgesic and hypotensive effects are also found; thus the directly measured blood pressure of conscious, spontaneously hypertonic rats having a catheter in place (strain SHR/NIH-MO/CHB-EMD; for method cf. Weeks and Jones, Proc. Soc. Exptl. Biol. Med. 104 (1960), (646–648) is lowered after intragastric administration of the compounds.

Compounds of the formula I and physiologically acceptable salts thereof can therefore be used as active compounds for medicaments and also as intermediate products for the preparation of other active compounds for medicaments.

In the acyloxy group by which the radical Ind is substituted "acyl" is the radical of an organic carboxylic or sulfonic acid having 1–12, preferably 1–7, C atoms, for example alkanoyl having 1–12, preferably 1–7 and especially 1–4, C atoms, such as formyl, acetyl, propionyl, butyryl, isobutyryl, valeryl, isovaleryl, 2-methylbutyryl, trimethylacetyl, caproyl, isocaproyl, tert.-butylacetyl, heptanoyl, octanoyl, nonanoyl, decanoyl, undecanoyl or dodecanoyl; cycloalkanoyl having 4–12, preferably 4–7 C atoms, such as cyclopropylcarbonyl, cyclobutylcarbonyl, cyclopentylcarbonyl, cyclohexylcarbonyl or cycloheptylcarbonyl; aroyl having 7–12, preferably 7–10, C atoms, such as benzoyl, o-, m- or p-toluyl, o-, m-, p-ethylbenzoyl, 1-naphthoyl or 2-napththoyl; aralkanoyl having 8–12 C atoms, for example phenylacetyl, 1-phenylpropionyl or 2-phenypropionyl; hetero-aroyl having 3–12, preferably 5–10, C atoms, such as nicotinoyl, isonicotinoyl, picolinoyl, thienyl-2-carbonyl, thienyl-3-carbonyl, furyl-2-carbonyl or furyl-3-carbonyl; alkanesulfonyl having 1–12, preferably 1–7 and especially 1–4, C atoms, such as methanesulfonyl, ethanesulfonyl, 1-propanesulfonyl or 2-propanesulfonyl; or arylsulfonyl having 6–12, preferably 6–10, C atoms, such as benzenesulfonyl, o-, m- or p-toluenesulfonyl, 1-naphthalenesulfonyl or 2-napthalenesulfonyl.

Thus, the acyl group can typically be derived from a hydrocarbon carboxylic or sulfonic acid of 1–12 C atoms and can also be derived from aromatic heterocyclic carboxylic or sulfonic acids of from 3–12 C atoms and from 4–13 total atoms, typically having 1–2 fused rings, each containing 4–6 ring atoms and each heteroacyl group containing 1–3 hetero atoms selected from O, N, or S.

The acyl groups mentioned can also be substituted. Thus the following are examples of suitable "acyl"; alkoxycarbonyl having 2–12, preferably 2–6, C atoms, such as methoxycarbonyl or ethoxycarbonyl; aryloxycarbonyl having 7–12, preferably 7–10, C atoms, such as phenoxycarbonyl; aralkoxycarbonyl; having 8–10 C atoms, such as benzenzyloxycarbonyl carbamoyl; monoalkylcarbamoyl and dialkylcarbamoyl having 2–12, preferably 2–6, C atoms, such as N-methylcarbamoyl, N,N-dimethylcarbamoyl or N,N-diethylcarbamoyl; alkoxyalkanoyl having 3–12, preferably 3–7, C atoms, such as methoxyacetyl, ethoxyacetyl, 1-methoxypropionyl or 2-methoxypropionyl; substituted, in particular monosubstituted to trisubstituted, aroyl having 7–12, preferably 7–10, C atoms, such as o-, m-or p-methoxybenzoyl, 3,4-dimethoxybenzoyl, 3,4,5-trimethoxybenzoyl, o-, m- or p-fluorobenzoyl, o-, m- p-chlorobenzoyl, o-, m- or p-nitrobenzoyl, o-, m- or p-dimethylaminobenzoyl.

Acyl is preferably alkanoyl having 1–4 C atoms, aroyl having 7–10 C atoms, alkanesulfonyl having 1–4 C atoms, arylsulfonyl having 6–10 C atoms or dialkylcarbamoyl having 3–6 C atoms.

The radical A is preferably —(CH$_2$)$_4$—, and also preferably —CH$_2$—S—CH$_2$CH$_2$—.

Accordingly, the parameter n is preferably 0.

The compounds of the formula I can contain one or more asymmetric carbon atoms. If several asymmetric carbon atoms are present, therefore, they can exist as racemates and also as mixtures of several racemates as well as in various optically active forms.

The invention also relates to a process for the preparation of the compounds of the formula I and of their salts, characterized in that a compound of the formula II Ind—A—X$^1$                II wherein
X¹ is X or NH₂ and
X is Cl, Br, I, OH or a reactive, functionally modified OH group and
Ind and A have the meanings indicated,
is reacted with a compound of the formula III

X²—CH₂CH₂—C(C₆H₅)=CHCH₂—X³     III wherein
X² and X³ can be identical or different and, if X¹ is NH₂, each is X, otherwise they are together NH, and
Z has the meaning indicated,
or a compound which otherwise corresponds to the formula I, but which contains one or more reducible group(s) and/or one or more additional C—C— and/or C—N— bond(s) instead of one or more hydrogen atoms, is treated with a reducing agent, or, in order to prepare thioethers of the formula I wherein
A is —CH₂—S—CH₂CH₂—, a compound of the formula IV Ind—CH₂N(R)₂     IV wherein
R is alkyl having 1-4 C atoms and both radicals R together are also —(CH₂)$_p$— or —CH₂CH₂OCH₂CH₂— and
p is 4 or 5 and
Ind has the meaning indicated,
is reacted with 1-(2-thioethyl)-4-phenyl-3,4-dehydropiperidine (V) or one of its salts, and/or, if appropriate, a thioether group in a compound of the formula I is oxidized to give an SO group or an SO₂ group or an SO group is oxidized to give an SO₂ group, and/or a resulting base of the formula I is converted into one of its acid addition salts by treatment with an acid.

The preparation of the compounds of the formula I is in other respects effected by methods which are in themselves known, such as are described in the literature (for example in standard works such as Houben-Weyl, Methoden der Organischen Chemie ("Methods of Organic Chemistry"), Georg-Thieme-Verlag, Stuttgart; or Organic Reactions, John Wiley & Sons, Inc., New York), specifically under reaction conditions such as are known and suitable for the reactions mentioned. In this regard it is also possible to make use of variants which are in themselves known but are not mentioned here in detail.

The starting materials for the process claimed can, if desired, also be formed in situ, in such a manner that they are not isolated from the reaction mixture, but are immediately reacted further to give the compounds of the formula I.

The hydroxyindole esters of the formula I are preferably obtainable by esterifying the corresponding hydroxyindoles. Some of these are known, for example from European Pat. No. 0,007,399 or European Pat. No. 0,105,397; those which are not known can readily be prepared analogously to those which are known, for example by reacting hydroxyindole derivatives corresponding to the formula Ind—A—X¹ wherein, however, the radical Ind is replaced by a 3-indolyl radical which is substituted in the 4-, 5-, 6- or 7-position by an HO group, with compounds of the formula III.

The esterification is preferably carried out by means of a reactive derivative of the corresponding acid, for example an anhydride, chloride or bromide. The reaction is carried out in the presence or absence of an inert solvent, for example a hydrocarbon, such as benzene or toluene, or a halogenated hydrocarbon, such as methylene dichloride, preferably with the addition of a base, such as sodium or potassium hydroxide solution or a tertiary amine, such as triethylamine, pyridine or 4-dimethylaminopyridine. It is also possible to use an excess of the base as the solvent. The reaction temperatures are preferably between 0° and 150°, in particular between 20° and 120°.

In the indole derivatives of the formula II, X¹ is preferably X; accordingly X² and X³ in the compounds of the formula III together are preferably NH. The radical X is preferably Cl or Br; it can, however, also be I, OH or a reactive, functionally modified OH group, in particular alkylsulfonyloxy having 1-6 C atoms (for example methanesulfonyloxy) or arylsulfonyloxy having 6-10 C atoms (for example benzenesulfonyloxy, p-toluenesulfonyloxy, 1-naphthalenesulfonyloxy or 2-naphthalenesulfonyloxy).

Accordingly, the indole derivatives of the formula I are obtainable, in particular, by reacting compounds of the formula Ind—A—Cl or Ind—A—Br with the compound of the formula III wherein X² and X³ together are an NH group (designated below as IIIa).

The compounds of the formulae II and III are in part known; the compounds of the formulae II and III which are not known can readily be prepared analogously to the known compounds. Compounds of the formula II (A=—CH₂—S—CH₂CH₂—) can be prepared, for example, from Mannich bases of the formula IV and thiols of the formula HS—CH₂CH₂—X¹, for example HS—CH₂CH₂OH. The sulfoxides and sulfones of the formula II (A=—CH₂—SO—CH₂CH₂— or —CH₂—SO₂—CH₂CH₂—) are accessible by oxidation of the thioethers (II, A=—CH₂—S—CH₂CH₂—). Primary alcohols of the formula Ind—A—OH can be obtained, for example, by esterification of the corresponding carboxylic acids and subsequent selective reduction or by selective esterification. Treatment with thionyl chloride, hydrogen bromide, phosphorus tribromide or similar halogen compounds affords the corresponding halides of the formula Ind—A—Hal. The corresponding sulfonyloxy compounds can be obtained from the alcohols Ind—A—OH by reacting the latter with the corresponding sulfonyl chlorides. The iodine compounds of the formula Ind—A—I can be obtained, for example, by the action of potassium iodide on the appropriate p-toluenesulfonic acid esters. The amines of the formula Ind—A—NH₂ can be prepared, for example, from the halides by means of potassium phthalimide or by reducing the corresponding nitriles.

The reaction of the compounds II and III takes place in accordance with methods such as are known from the literature for the alkylation of amines. The components can be melted together in the absence of a solvent, if appropriate in a sealed tube or in an autoclave. It is also possible, however, to react the compounds in the presence of an inert solvent. Examples of suitable solvents are hydrocarbons, such as benzene, toluene, xylene; ketones, such as acetone or butanone; alcohols, such as methanol, ethanol, isopropanol or n-butanol; ethers, such as tetrahydrofuran (THF) or dioxane; amides, such as dimethylformamide (DMF) or N-methylpyrrolidone; nitriles, such as acetonitrile, and also, if appropriate, mixtures of these solvents with one another or mixtures with water. The addition of an acid-binding agent, for example an alkali metal hydroxide, carbonate or bicarbonate or an alkaline earth metal hydroxide, carbonate or bicarbonate or another salt of the alkali or alkaline earth metals, preferably potassium, sodium or calcium, with a weak acid, or the addition of an organic base, such as triethylamine, dimethylaniline, pyridine or quinoline, or an excess of the amine component Ind—A—NH$_2$ or IIIa can be favourable. Depending on the conditions used, the reaction time is between a few minutes and 14 days, while the reaction temperatures are between about 0° and 150°, normally between 20° and 130°.

It is also possible to obtain a compound of the formula I by treating a precursor containing one or more reducible group(s) and/or one or more additional C—C— and/or C—N— bond(s) instead of hydrogen atoms, with a reducing agent, preferably at temperatures between −80° and +250° in the presence of at least one inert solvent.

Reducible (replaceable by hydrogen) groups are, in particular, oxygen in a carbonyl group, hydroxyl, arylsulfonyloxy (for example p-toluenesulfonyloxy), N-benzenesulfonyl, N-benzyl or O-benzyl.

Thus, for example, a reduction of pyridinium salts of the formula VI

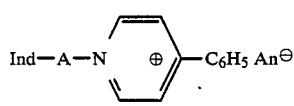

wherein An is an anion, preferably Cl, Br or CH$_3$SO$_3$ to give compounds of the formula I can be effected, for example, by means of NaBH$_4$ in water, methanol or ethanol or in mixtures of these solvents, if desired with the addition of a base such as NaOH, at temperatures between about 0° and 80°.

Indole derivatives of the formula I (A=—CH$_2$—S—CH$_2$CH$_2$—) can also be obtained by reacting Mannich bases of the formula IV with the thiol of the formula V (or salts thereof).

The starting materials of the formulae IV and V are in part known; those of these starting materials which are not known can readily be prepared analogously to the known compounds. Thus the Mannich bases of the formula IV are obtainable, for example, from indoles of the formula Ind—H, formaldehyde and amines of the formula HN(R)$_2$, and the thiol V is obtainable from IIIa and thiol derivatives of the formula HS—CH$_2$—CH$_2$—X$^1$ (it being also possible to protect the HS group in the intermediate stage).

Specifically, the reaction of IV with V in the presence or absence of an inert solvent is effected at temperatures between about −20° and 250°, preferably between 60° and 150°. Examples of suitable solvents are hydrocarbons, such as benzene, toluene, xylenes or mesitylene; tertiary bases, such as triethylamine, pyridine or picolines; alcohols, such as methanol, ethanol or butanol; glycols and glycol ethers, such as ethylene glycol, diethylene glycol or 2-methoxyethanol; ketones, such as acetone; ethers, such as THF or dioxane; amides, such as DMF; sulfoxides, such as dimethyl sulfoxide; or aqueous sodium hydroxide solution. Mixtures of these solvents are also suitable. The thiol V is preferably first converted into one of the corresponding mercaptides, preferably into the corresponding sodium or potassium mercaptide by reaction with sodium hydroxide, potassium hydroxide, sodium ethylate or potassium ethylate.

It is also possible, if desired, to convert a compound of the formula I into another compound of the formula I by methods which are in themselves known.

Thus the thioether group in a thioether of the formula I (A=—CH$_2$—S—CH$_2$CH$_2$—) can be oxidized to give an SO group or an SO$_2$ group, or the SO group in a sulfoxide of the formula I (A=—CH$_2$—SO—CH$_2$CH$_2$) can be oxidized to give an SO$_2$ group. If it is desired to obtain the sulfoxides, oxidation is carried out with, for example, hydrogen peroxide, per-acids, such as m-chloroperbenzoic acid, Cr(VI) compounds, such as chromic acid, KMnO$_4$, 1-chlorobenzotriazole, Ce(IV) compounds, such as (NH$_4$)$_2$Ce(NO$_3$)$_6$, aromatic diazonium salts having negative substituents, such as o-nitrophenyldiazonium or p-nitrophenyldiazonium chloride, or by electrolytic means under relatively mild conditions and at relatively low temperatures (about −80° to +100°). If, on the other hand, it is desired to obtain the sulfones (from the thioethers or the sulfoxides), the same oxidizing agents are used under more vigorous conditions and/or in excess and, as a rule, at higher temperatures. The customary inert solvents can be present or absent in these reactions. Examples of suitable inert solvents are water, aqueous mineral acids, aqueous alkali metal hydroxide solutions, lower alcohols, such as methanol or ethanol, esters, such as ethyl acetate, ketones, such as acetone, lower carboxylic acids, such as acetic acid, nitriles, such as acetonitrile, hydrocarbons, such as benzene, or chlorinated hydrocarbons, such as chloroform or CCl$_4$. 30% aqueous hydrogen peroxide is a preferred oxidizing agent. When used in the calculated amount in solvents such as acetic acid, acetone, methanol, ethanol or aqueous sodium hydroxide solution at temperatures between −20° and 100°, this results in the sulfoxides, or, when used in excess at higher temperatures, preferably in acetic acid or in a mixture of acetic acid and acetic anhydride, it results in the sulfones.

A resulting base of the formula I can be converted into the appropriate acid addition salt by means of an acid. Acids suitable for this reaction are those which afford physiologically acceptable salts. Thus it is possible to use inorganic acids, for example sulfuric acid, hydrogen halide acids, such as hydrochloric acid or hydrobromic acid, phosphoric acids, such as orthophosphoric acid, nitric acid or sulfamic acid, and also organic acids, specifically aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic or naphthalenedisulfonic acids or laurylsulfuric acid. Salts with physiologically unacceptable acids, for example picrates, can be used for isolating or purifying the compounds of the formula I.

The free bases of the formula I can, if desired, be liberated from their salts by treatment with strong bases, such as sodium hydroxide or carbonate or potassium hydroxide or carbonate.

The compounds of the formula I and their physiologically acceptable salts can be used for the preparation of pharmaceutical formulations, in particular by non-chemical means. In this regard they can be brought into a suitable dosage form together with at least one solid, liquid or semi-liquid excipient or auxiliary and, if desired, in combination with one or more further active compound(s).

The invention also relates to agents, in particular pharmaceutical formulations, containing at least one compound of the formula I and/or one of its physiologically acceptable salts. These formulations can be employed as medicaments in human or veterinary medicine. Suitable excipients are organic or inorganic substances which are suitable for enteral (for example oral) or parenteral administration or for topical application and which do not react with the new compounds, for example water, vegetable oils, benzyl alcohols, polyethylene glycols, gelatine, carbohydrates, such as lactose or starch, magnesium stearate, talc or petroleum jelly. Tablets, coated tablets, capsules, syrups, elixirs, drops or suppositories are particularly suitable for enteral administration, solutions, preferably oily or aqueous solutions, and also suspensions, emulsions or implants are particularly suitable for parenteral administration, and ointments, creams or powders are particularly suitable for topical application. The new compounds can also be lyophilized, and the resulting lyophilizates can be used, for example, for the production of injection preparations. The formulations indicated can be sterilized and/or can contain auxiliaries, such as lubricants, preservatives, stabilizing and/or wetting agents, emulsifiers, salts for influencing the osmotic pressure, buffer substances, colorants, flavourings and/or aroma substances. If desired, they can also contain one or more further active compounds, for example one or more vitamins.

The compounds of the formula I and their physiologically acceptable salts can be administered to humans or animals, in particular mammals, such as monkeys, dogs, cats, rats or mice, and can be used in the therapeutic treatment of the human or animal body and in combating diseases, particularly in the therapy of Parkinson's disease, of extrapyramidal disorders in the therapy of neuroleptic complaints, of depressions and/or psychoses and of side effects in the treatment of hypertension (for example with α-methyldopa). The compounds can also be used in endocrinology and gynaecology, for example for the therapy of acromegaly, hypogonadism, secondary amenorrhoea, premenstrual syndrome, undesired puerperal lactation and, in general, as a prolactin inhibitor, and also for the therapy of cerebral disorders (for example migraine), particularly in geriatrics in a manner similar to that of certain ergot alkaloids, and also for lowering blood pressure.

In this regard, the substances according to the invention are administered, as a rule, analogously to know commercial perparations (for example bromocriptine or dihydroergocornine), preferably in dosages of about 0.1 to 50 mg, in particular about 0.1 to 5 mg, per dosage unit. The daily dosage is preferably about 0.0005 to 1 mg/kg of body weight. Preferred dosages ranges for specific indications are as follows: parkinsonism 0.2 to 5, preferably 0.5 to 2; dyskinesia 0.2 to 5, preferably 0.5 to 2; psychosis, e.g. chronic schizophrenia, 0.1 to 5, preferably 0.1 to 2; acromegaly 0.1 to 5, preferably 0.1 to 2; migraine 0.1 to 1, preferably 0.1 to 0.5 mg per dosage unit. The particular dose for each specific patient depends, however, on a very wide variety of factors, for example on the effectiveness of the particular compound employed, on the age, body weight, general state of health and sex, on the diet, on the time and means of administration, on the rate of excretion, the combination of medicaments and the severity of the particular disease to which the therapy relates. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight; unless otherwise indicated.

In the examples below, "customary working up" means as follows: if necessary, water is added, the mixture is extracted with methylene dichloride, the phases are separated, the organic phase is dried over sodium sulfate filtered and evaporated and the residue is purified by chromatography over silica gel and/or by crystallization. Rf values were determined by thin layer chromatography over silica gel.

EXAMPLE 1

10.5 ml of acetic anhydride are added dropwise to a solution of 34.6 g of 3-[4-(4-phenyl-3,4-dehydro-1-piperidyl)-butyl]-5-hydroxyindole in 175 ml of pyridine, the mixture is heated on a steam bath for 30 minutes, poured into 1.7 ml of water and stirred for a further hour, and the resulting 3-[4-(4-phenyl-3,4-dehydro-1-piperidyl)-butyl]-5-acetoxyindole ("A") is filtered off, melting point 120°–122° (from isopropanol).

The following 3-[4-(4-phenyl-3,4-dehydro-1-piperidyl)-butyl]-indoles are obtained analogously using the anhydrides, chlorides or bromides of the corresponding acids:

3-[4-(4-phenyl-3,4-dehydro-1-piperidyl)-butyl]-4-acetoxyindole
3-[4-(4-phenyl-3,4-dehydro-1-piperidyl)-butyl]-6-acetoxyindole
3-[4-(4-phenyl-3,4-dehydro-1-piperidyl)-butyl]-7-acetoxyindole
3-[4-(4-phenyl-3,4-dehydro-1-piperidyl)-butyl]-5-propionyloxyindole
3-[4-(4-phenyl-3,4-dehydro-1-piperidyl)-butyl]-5-butyryloxyindole
3-[4-(4-phenyl-3,4-dehydro-1-piperidyl)-butyl]-5-isobutyryloxyindole
3-[4-(4-phenyl-3,4-dehydro-1-piperidyl)-butyl]-5-valeryloxyindole
3-[4-(4-phenyl-3,4-dehydro-1-piperidyl)-butyl]-5-isolvaleryloxyindole
3-[4-(4-phenyl-3,4-dehydro-1-piperidyl)-butyl]-5-(2-methylbutyrloxy)-indole
3-[4-(4-phenyl-3,4-dehydro-1-piperidyl)-butyl]-5-trimethylacetoxyindole
3-[4-(4-phenyl-3,4-dehydro-1-piperidyl)-butyl]-5-caproyloxyindole
3-[4-(4-phenyl-3,4-dehydro-1-piperidyl)-butyl]-5-heptanoyloxyindole
3-[4-(4-phenyl-3,4-dehydro-1-piperidyl)-butyl]-5-octanoyloxyindole
3-[4-(4-phenyl-3,4-dehydro-1-piperidyl)-butyl]-5-nonanoyloxyindole 3-[4-(4-phenyl-3,4-dehydro-1-piperidyl)-butyl]-5-decanoyloxyindole
3-[4-(4-phenyl-3,4-dehydro-1-piperidyl)-butyl]-5-undecanoyloxyindole
3-[4-(4-phenyl-3,4-dehydro-1-piperidyl)-butyl]-5-dodecanoyloxyindole
3-[4-(4-phenyl-3,4-dehydro-1-piperidyl)-butyl]-5-cyclohexylcarbonyloxyindole
3-[4-(4-phenyl-3,4-dehydro-1-piperidyl)-butyl]-5-benzoyloxyindole, hydrochloride-hydrate, m.p. 106° (decomp.)
3-[4-(4-phenyl-3,4-dehydro-1-piperidyl)-butyl]-5-p-toluyloxyindole
3-[4-(4-phenyl-3,4-dehydro-1-piperidyl)-butyl]-5-methoxybenzoyloxyindole
3-[4-(4-phenyl-3,4-dehydro-1-piperidyl)-butyl]-5-phenylacetoxyindole
3-[4-(4-phenyl-3,4-dehydro-1-piperidyl)-butyl]-4-methanesulfonyloxyindole
3-[4-(4-phenyl-3,4-dehydro-1-piperidyl)-butyl]-5-methanesulfonyloxyindole, hydrochloride, m.p. 208°–210°
3-[4-(4-phenyl-3,4-dehydro-1-piperidyl)-butyl]-6-methanesulfonyloxyindole
3-[4-(4-phenyl-3,4-dehydro-1-piperidyl)-butyl]-7-methanesulfonyloxyindole
3-[4-(4-phenyl-3,4-dehydro-1-piperidyl)-butyl]-5-ethanesulfonyloxyindole
3-[4-(4-phenyl-3,4-dehydro-1-piperidyl)-butyl]-4-benzenesulfonyloxyindole
3-[4-(4-phenyl-3,4-dehydro-1-piperidyl)-butyl]-5-benzenesulfonyloxyindole
3-[4-(4-phenyl-3,4-dehydro-1-piperidyl)-butyl]-6-benzenesulfonyloxyindole
3-[4-(4-phenyl-3,4-dehydro-1-piperidyl)-butyl]-7-benzenesulfonyloxyindole
3-[4-(4-phenyl-3,4-dehydro-1-piperidyl)-butyl]-4-p-toluenesulfonyloxyindole
3-[4-(4-phenyl-3,4-dehydro-1-piperidyl)-butyl]-5-p-toluenesulfonyloxyindole, hydrochloride, m.p. 226°–228°
3-[4-(4-phenyl-3,4-dehydro-1-piperidyl)-butyl]-6-p-toluenesulfonyloxyindole
3-[4-(4-phenyl-3,4-dehydro-1-piperidyl)-butyl]-7-p-toluenesulfonyloxyindole
3-[4-(4-phenyl-3,4-dehydro-1-piperidyl)-butyl]-5-N,N-dimethylcarbamoyloxyindole
3-[4-(4-phenyl-3,4-dehydro-1-piperidyl)-butyl]-5-N,N-diethylcarbamoyloxyindole
3-[4-(4-phenyl-3,4-dehydro-1-piperidyl)-butyl]-5-N,N-dipropylcarbamoyloxyindole.

EXAMPLE 2

A solution of 2.66 g of 3-(4-chlorobutyl)-5-acetoxyindole (or 3.10 g of 3-(4-bromobutyl)-5-acetoxyindole) and 1.6 g of 4-phenyl-3,4-dehydropiperidine (IIIa) in 10 ml of acetonitrile is stirred for 12 hours at 20° and the mixture is worked up in the customary manner to give "A", melting point 120°–122°.

EXAMPLE 3

A mixture of 2.46 g of 3-(4-aminobutyl)-5-acetoxyindole [obtainable by reacting 3-(4-bromobutyl)-5-acetoxyindole with potassium phthalimide and subsequently hydrolyzing the product] and 2.15 g of 1,5-dichloro-3-phenyl-2-pentene in 40 ml of acetone and 40 ml of water is boiled for 24 hours and worked up in the customary manner. "A" is obtained, melting point 120°–122°.

EXAMPLE 4

10 g of NaBH$_4$ in 200 ml of water are added, with stirring, to a solution of 46.5 g of 1-[4-(5-acetoxy-3-indolyl)-butyl]-4-phenylpyridinium bromide [obtainable from 4-phenylpyridine and 3-(4-bromobutyl)-5-acetoxyindole] in 500 ml of aqueous 1N NaOH, and the mixture is then stirred for a further 3 hours at 60°. Working up in the customary manner gives "A", melting point 120°–122°.

EXAMPLE 5

2.76 g of Na are dissolved in 180 ml of ethanol, 21.9 g of 1-(2-mercaptoethyl)-4-phenyl-3,4-dehydropiperidine and 23.2 g of 5-acetoxygramine (obtainable from 5-acetoxyindole, HCHO and dimethylamine) are added, and the mixture is boiled for 16 hours and evaporated and the residue is worked up in the customary manner to give 3-[2-thia-4-(4-phenyl-3,4-dehydro-1piperidyl)-butyl[-5-acetoxyindole.

The following 3-[2-thia-4-(4-phenyl-3,4-dehydro-1-piperidyl)-butyl]-indoles are obtained analogously from the corresponding gramine derivatives:
3-[2-thia-4-(4-phenyl-3,4-dehydro-1-piperidyl)-butyl]-4-acetoxyindole
3-[2-thia-4-(4-phenyl-3,4-dehydro-1-piperidyl)-butyl]-6-acetoxyindole
3-[2-thia-4-(4-phenyl-3,4-dehydro-1-piperidyl)-butyl]-7-acetoxyindole
3-[2-thia-4-(4-phenyl-3,4-dehydro-1-piperidyl)-butyl]-5-propionyloxyindole
3-[2-thia-4-(4-phenyl-3,4-dehydro-1-piperidyl)-butyl]-5-butyryloxyindole
3-[2-thia-4-(4-phenyl-3,4-dehydro-1-piperidyl)-butyl]-5-isobutyryloxyindole
3-[2-thia-4-(4-phenyl-3,4-dehydro-1-piperidyl)-butyl]-5-valeryloxyindole
3-[2-thia-4-(4-phenyl-3,4-dehydro-1-piperidyl)-butyl]-5-isovaleryloxyindole
3-[2-thia-4-(4-phenyl-3,4-dehydro-1-piperidyl)-butyl]-5-(2-methylbutyryloxy)-indole
3-[2-thia-4-(4-phenyl-3,4-dehydro-1-piperidyl)-butyl]-5-trimethylacetoxyindole
3-[2-thia-4-(4-phenyl-3,4-dehydro-1-piperidyl)-butyl]-5-caproyloxyindole
3-[2-thia-4-(4-phenyl-3,4-dehydro-1-piperidyl)-butyl]-5-heptanoyloxyindole
3-[2-thia-4-(4-phenyl-3,4-dehydro-1-piperidyl)-butyl]-5-octanoyloxyindole
3-[2-thia-4-(4-phenyl-3,4-dehydro-1-piperidyl)-butyl]-5-nonanoyloxyindole
3-[2-thia-4-(4-phenyl-3,4-dehydro-1-piperidyl)-butyl]-5-decanoyloxyindole
3-[2-thia-4-(4-phenyl-3,4-dehydro-1-piperidyl)-butyl]-5-undecanoyloxyindole
3-[2-thia-4-(4-phenyl-3,4-dehydro-1-piperidyl)-butyl]-5-dodecanoyloxyindole
3-[2-thia-4-(4-phenyl-3,4-dehydro-1-piperidyl)-butyl]-5-cyclohexycarbonyloxyindole
3-[2-thia-4-(4-phenyl-3,4-dehydro-1-piperidyl)-butyl]-5-benzoyloxyindole
3-[2-thia-4-(4-phenyl-3,4-dehydro-1-piperidyl)-butyl]-5-p-toluyloxyindole
3-[2-thia-4-(4-phenyl-3,4-dehydro-1-piperidyl)-butyl]-5-p-methoxybenzoyloxyindole
3-[2-thia-4-(4-phenyl-3,4-dehydro-1-piperidyl)-butyl]-5-phenylacetoxyindole 3-[2-thia-4-(4-phenyl-3,4-dehydro-1-piperidyl)-butyl]-4-methanesulfonyloxyindole
3-[2-thia-4-(4-phenyl-3,4-dehydro-1-piperidyl)-butyl]-5-methanesulfonyloxyindole
3-[2-thia-4-(4-phenyl-3,4-dehydro-1-piperidyl)-butyl]-6-methanesulfonyloxyindole
3-[2-thia-4-(4-phenyl-3,4-dehydro-1-piperidyl)-butyl]-7-methanesulfonyloxyindole
3-[2-thia-4-(4-phenyl-3,4-dehydro-1-piperidyl)-butyl]-5-ethanesulfonyloxyindole
3-[2-thia-4-(4-phenyl-3,4-dehydro-1-piperidyl)-butyl]-4-benzenesulfonyloxyindole
3-[2-thia-4-(4-phenyl-3,4-dehydro-1-piperidyl)-butyl]-5-benzenesulfonyloxyindole
3-[2-thia-4-(4-phenyl-3,4-dehydro-1-piperidyl)-butyl]-6-benzenesulfonyloxyindole
3-[2-thia-4-(4-phenyl-3,4-dehydro-1-piperidyl)-butyl]-7-benzenesulfonyloxyindole
3-[2-thia-4-(4-phenyl-3,4-dehydro-1-piperidyl)-butyl]-4-p-toluenesulfonyloxyindole
3-[2-thia-4-(4-phenyl-3,4-dehydro-1-piperidyl)-butyl]-5-p-toluenesulfonyloxyindole
3-[2-thia-4-(4-phenyl-3,4-dehydro-1-piperidyl)-butyl]-6-p-toluenesulfonyloxyindole
3-[2-thia-4-(4-phenyl-3,4-dehydro-1-piperidyl)-butyl]-7-p-toluenesulfonyloxyindole
3-[2-thia-4-(4-phenyl-3,4-dêhydro-1-piperidyl)-butyl]-5-N,N-dimethylcarbamoyloxyindole
3-[2-thia-4-(4-phenyl-3,4-dehydro-1-piperidyl)-butyl]-5-N,N-diethylcarbamoyloxyindole
3-[2-thia-4-(4-phenyl-3,4-dehydro-1-piperidyl)-butyl]-5-N,N-dipropylcarbamoyloxyindole.

EXAMPLE 6

6 ml of 30% $H_2O_2$ are added to a boiling solution of 4.06 g of 3-[2-thia-4-(4-phenyl-3,4-dehydro-1-piperidyl)-butyl]-5-acetoxyindole in 50 ml of ethanol, and the mixture is then boiled for 3 hours. After a further 4 ml of the oxidizing agent has been added, the mixture is boiled for a further 9 hours and cooled, and the residue is worked up in the customary manner to give 3-[2-thia-4-(4-phenyl-3,4-dehydro-1-piperidyl)-butyl]-5-acetoxyindole S-oxide.

EXAMPLE 7

9 ml of 30% $H_2O_2$ are added to a solution of 4.06 g of 3-[2-thia-4-(4-phenyl-3,4-dehydro-1-piperidyl)-butyl]-5-acetoxyindole in 25 ml of acetic acid, and the mixture is boiled for 90 minutes. Working up in the customary manner gives 3-[2-thia-4-(4-phenyl-3,4-dehydro-1-piperidyl)-butyl]-5-acetoxyindole S,S-dioxide.

The examples below relate to pharmaceutical formulations containing amines of the formula I or acid addition salts thereof:

EXAMPLE A: TABLETS

A mixture of 1 kg of 3-[4-(4-phenyl-3,4-dehydro-1-piperidyl)-butyl]-5-acetoxyindole, 4 kg of lactose, 1.2 kg of potato starch, 0.2 kg of talc and 0.1 kg of magnesium stearate is compressed in a customary manner to give tablets in such a manner that each tablet contains 10 mg of active compound.

EXAMPLE B: COATED TABLETS

Tablets are compressed analogously to Example A and are then coated in a customary manner with a coating of sucrose, potato starch, talc, tragacanth and colorant.

EXAMPLE C: CAPSULES 2 kg of 3-[4-(4-phenyl-3,4-dehydro-1-piperidyl)-butyl]-5-acetoxyindole are filled in a customary manner into hard gelatine capsules in such a manner that each capsule contains 20 mg of the active compound.

EXAMPLE D: AMPOULES

A solution of 1 kg of 3-[4-(4-phenyl-3,4-dehydro-1-piperidyl)-butyl]-5-acetoxyindole in 30 l of twice distilled water is filtered under sterile conditions, filled into ampoules and lyophilized and closed under sterile conditions. Each ampoule contains 10 mg of active compound.

Tablets, coated tablets, capsules and ampoules containing one or more of the remaining active compounds of the formula I and/or physiologically acceptable acid addition salts thereof are obtainable analogously.

In the ligand binding test (method cf. Creese et al., l.c.) with tritiated spiperone on striatal membrane preparations of rats, the following 3-[4-(4-phenyl-3,4-dehydro-1-piperidyl)-butyl]-indoles were found to be particularly effective ([$^3$H]-spiperone binding at $10^7$ mole·1$^{-1}$ lower than 25%, with respect to control values being defined as 100%):

5-p-toluenesulfonyloxy-
5-methanesulfonyloxy-
5-acetoxy-
5-N,N-dimethylcarbamoyloxy.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A hydroxyindole ester of the formula

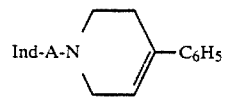

wherein
Ind is 3-indolyl substituted in the 5-position by acyloxy, wherein acyl is $C_{1-4}$-alkanoyl or benzoyl,
A is —$(CH_2)_4$—, and
—$C_6H_5$ is phenyl, or a physiologically acceptable salt thereof.

2. 3-[4-(4-Phenyl-3,4-dehydro-1-piperidyl)-butyl]-5-acetoxyindole, a compound of claim 1.

3. A pharmaceutical composition comprising an amount of a compound of claim 1 effective to exert a dopamine stimulating effect and a pharmaceutically acceptable carrier.

4. A pharmaceutical composition comprising from about 0.2 to about 500 mg of a compound of claim 1 and a pharmaceutically acceptable carrier.

5. A method of treating a disorder which is treatable by an agent having dopamine-stimulating activity comprising administering an amount of a compound of claim 1 effective to exert a dopamine-stimulating effect.

6. A method of treating Parkinson's disease in a patient comprising administering an amount of a compound of claim 1 effective to treat Parkinson's disease.

7. A method of treating psychosis comprising administering a compound of claim 1 in an amount effective to achieve an antipsychotic effect.

8. A compound of claim 1 wherein acyl is $C_{1-4}$ alkanoyl.

* * * * *